United States Patent [19]

Hollingsworth

[11] Patent Number: Plant 5,718

[45] Date of Patent: Apr. 15, 1986

[54] PEONY PLANT

[76] Inventor: Donald Hollingsworth, 5831 N. Colrain Ave., Kansas City, Mo. 64151

[21] Appl. No.: 635,497

[22] Filed: Jul. 30, 1984

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Arvid V. Zuber

[57] ABSTRACT

The present invention is a new and distinct cultivar of peony plant, a hybrid between three species, two shrubby and one herbaceous species, of the genus Paeonia, interspecific hybrid (*Paeonia lactiflora*×(*P. lutea*×*P. suffruticosa*), combination of species now known as Itoh Hybrids. The present cultivar's uniqueness is characterized by its outstanding yellow color with a superior tree peony flower type on a singularly healthy herbaceous plant, its excellent hardiness of flower buds and consequent reliability of flowering in relatively extreme climates, and, by its distinctive foliage and plant habit.

1 Drawing Figure

1

The present invention is a new and distinct cultivar of peony plant, a hybrid between three species, two shrubby and one herbaceous species, of the genus Paeonia, interspecific hybrid (*Paeonia lactiflora*×(*P. lutea*×*P. suffruticosa*), combination of species now known as Itoh Hybrids, named for the man who first discovered the cross in Japan. This cross has proven difficult to make and ornamentally appealing plants have been rare among its progeny, a large proportion of the seedlings showing more or less severe faults of abbreviated petal formation and disease-prone foliage. The applicant cultivar's uniqueness is characterized by its outstanding yellow color with a superior tree peony flower type on a singularly healthy herbaceous plant, its excellent hardiness of flower buds and consequent reliability of flowering in relatively extreme climates, and, by its distinctive foliage and plant habit.

This peony was originated by me at the farmyard of my parents-in-law near Maryville, Mo. in 1969. The pollen (male) parent was Paeonia (Lutea Hybrids) 'Alice Harding', an $F_1$ hybrid shrubby peony with half-hardy perennial stems, a vigorous, healthy grower of low, spreading habit, having yellow double flowers with distinctive red flares at the petal bases, and with flowers held on relatively short, sagging stems resulting in poor presentation of the flowers, generally being covered by the typically luxuriant foliage. The pod (female) parent was a Chinese peony (*Paeonia lactiflora*) cultivar of which no record or tradition of a cultivar name now exists, now known as 'Carr East #2' for my purposes. It is a distinctively durable plant with long lasting, blush colored, anemone type flowers and shows outstanding health, being of a sort that is widely seen around old homesites, having persisted in place for many years, often under indifferent or no care.

The hybridization was accomplished by hand pollination. The seed was germinated under my personal care and the plant first grew in 1970. First flowering occurred in 1973 at which time it was observed to be a superior plant and was selected for further evaluation. The applicant plant is a unique clone and it has been propagated asexually for the past 11 years both by grafting of crown bud scions onto nurse root pieces and by division.

2

The applicant plant shows phenotypically that its prominent characteristics are the result of especially fortuitous segregation of the gene complements of its respective parents leading to an exceptionally favorable combination of characteristics in this individual.

The yellow flower color is of the strong, persistent hue found in plants of the half-hardy *Paeonia lutea* ancestor and hybrid descendants of that species. This yellow hue is reported to be due to the presence of one or more yellow carotenoid pigments, as contrasted to the paler, creamier yellows of flavenoid compounds found in yellow flowered descendants of certain herbaceous species. The strong yellow color of the applicant flower is further enhanced by a prominent red flare at the base of each petal. There is also a faint suffusion of the same red pigment throughout the petals upon flower opening, of the color pattern known as blush, which in this individual imparts a golden cast to the newly opened flower. This blush fades as the flower ages, leaving a clearer yellow petal hue at the end. According to The Royal Horticultural Society Colour Chart, a standard reference, the petal color upon opening is approximately 8B to 6C, passing to 4B at petal fall.

The flower type of the applicant plant is characteristic of many cultivars of the Japanese tree peonies (*Paeonia suffruticosa*), a symmetrically sculptured semi-double to open double form. It is made up of two to three rows of larger outer petals surrounding, in order, smaller inner petals, stamens and a prominent center composed of large, closely set green carpels, topped by large, curving, pink stigmas and encircled by a deeply incised sheath of a pale creamy, greenish color. The stamens are generally pale yellow with a red flush at the filament bases and, occasionally, a small amount of pollen imparts a spot of stronger yellow in the anther cases. The larger petals are consistently well formed to the petal end as contrasted to petal edges seen in some others of the introduced Itoh Hybrid cultivars. The number of the smaller petals present in an individual flower varies inversely with the number of stamens, these smaller petals apparently being formed from stamen initials during development of the flower bud, the transformation occuring sequentially beginning with outer segments and progressing inwardly along the phylotactic spiral, so that there is an abrupt change from petal segments to stamen segments contributing a characteristic tree peony flower type. This variable degree of stamen transformation results in the variable degree of doubling seen among the flowers. The number of petals has been seen to vary from approximately 20 to 50 or more.

The applicant cultivar opens its flowers over a period that is approximately two and one-half weeks in duration with little diminution in flower size or flower quality as the period progresses, in contrast to the shorter flowering period which is typical of individual cultivars of the Chinese peonies and the Japanese tree peonies. The flowers are produced one to three per stem with both the terminal and axillary buds produced on relatively long peduncles, suitable for cutting individually. There is seldom any benefit to be obtained from removal of side buds ("disbudding", as commonly practiced in producing Chinese peony flowers). The flowers are held well out from the foliage, unlike the pollen parent habit and that of many others of the Lutea Hybrids group, which have been the principal source of strong yellow flower color in garden peonies. Flowering stem posture ranges from approximately vertical to approximately horizontal in a mature plant, resulting in a relatively more favorable display of the flowers than is usually seen in the presently available yellow flowered peonies. Flower size is large, ranging six to eight inches in diameter from mature plants under good cultivation.

The applicant plant has flowered young and reliably from year to year at trial locations ranging from Missouri to the Northern teir of States in the United States. The herbaceous stems originate each spring from the below-ground overwintering buds, which have proven to be perfectly hardy wherever tested during the past 11 years. This is in contrast to the sometimes irregular performance of the similarly yellow-flowered Lutea Hybrid peonies in which half-hardy perennial stems are often killed in colder climates and only some of which can be expected to flower prolifically or dependably from below-ground overwintering buds.

The applicant plant is a medium height, broad plant having relatively large and cool green leaflets which have more frequently incised margins than is common among other garden peonies. The plant presents a relatively heavy texture in the landscape, for its overall dimensions, compared to most other herbaceous perennials. Plant height is about 24 inches and width ranges with maturity to 40 inches or more. Leaflets are smooth, dark green above—137A on The Royal Horticultural Society color scale—and 138B on the lower surface. Leaflet shape is similar to that of the Lutea Hybrid pollen parent, apices acuminate, margins more or less deeply incised, retaining this character from the *Paeonia lutea* ancestor. Large leaves are twice ternately divided to the mid-rib and there is a tendency of the two deepest incisions of the leaflet margins to form a partial third level of ternate division, as is characteristic of the genus. The applicant plant is considered to be an extremely useful landscape plant both for its flowering qualities and its season-long interest as a transitional form between low to medium woody plants and finer textured herbaceous perennials or in other applications where a relatively heavy plant of the size is desired.

Therefore the applicant plant is considered unique because of flower form, the hue of its flower petals, the dependability of its flower performance in a range of climates, the length of its flowering period, its superior plant habit and its overall landscape appeal.

The accompanying illustration is reproduced from an original photograph of the applicant plant, the color being as reasonably true as is possible in a color illustration of this character.

SUMMARY

Parentage:

*Seed parent.*—'Carr East #2' (non-patent).

*Pollen parent.*—Paeonia (Lutea Hybrid) 'Alice Harding' (non-patent).

Flower:

*Blooming habit.*—Annually, long flowering, considered late season.

*Bud.*—Size 13 Large. Form — Ovate, smooth and somewhat pointed. Color — Petals 8B–6C as first color shows. Sepals — Very smooth, soft green with wash of pink at edges, speckles of brownish green. Calyx — Polysepalous. Peduncle — To 10 inches length on both terminal and axillary flowers; colored like the sepals. Opening — Easily, a dependable performer.

*Bloom.*—Size — Large, 6–8 inches diameter. Borne — Singly, one main bud per penduncle. Form — Tree peony type semi-double, progressively transformed stamen segments form inner petals. Petalage — Double. Color — Petals 8B to 6C at earliest expansion, passing to 4B at petal fall. Variegations —0 Red flares at the bases of petals and filaments surround pale green and pink center.

*Petals.*—Texture — Thick, plump. Appearance — Cupped, ruffled and exotic. Form — Ruffled, sometimes crenulate edges. Arrangement — Imbricate. Persistence — Above average. Fragrance — Mild lemon fragrance, from *Paeonia lutea.* Lastingness — Above average.

*Genital organs.*—Stamens — Anthers and filaments present. Pollen — Present in small amounts, viability poor to none. Styles, stigmas ovaries — present, no fertility seen. Fruit — Develops without seed formation.

*Plant.*—Form: Bush, medium height, wider than tall in mature plant. Growth: Healthy, strong, vigorous. Foliage: Leaflets — 9, occasionally more. Size — Large compound leaf. Quantity — Moderate number of leaves. Color — 137A on upper surface, 138B underside. Shape — Bi-ternately compound; leaflets widely elliptic, margins smoothly incised, apices acuminate. Texture — Smooth, with lustrous surface. Margins — Smooth, no serration. Leaf stem — Thick, hard. Stipules — None. Disease resistance — Resistant to leaf spot and other leaf and crown diseases as observed in the originators garden; no unfavorable observations reported from other trial sites.

I claim:

1. A new and distinct peony plant cultivar of Itoh hybrid peony characterized by its rare yellow color, flower form, dependability of flowering, length of flowering period and superior plant habit, substantially as shown and described.

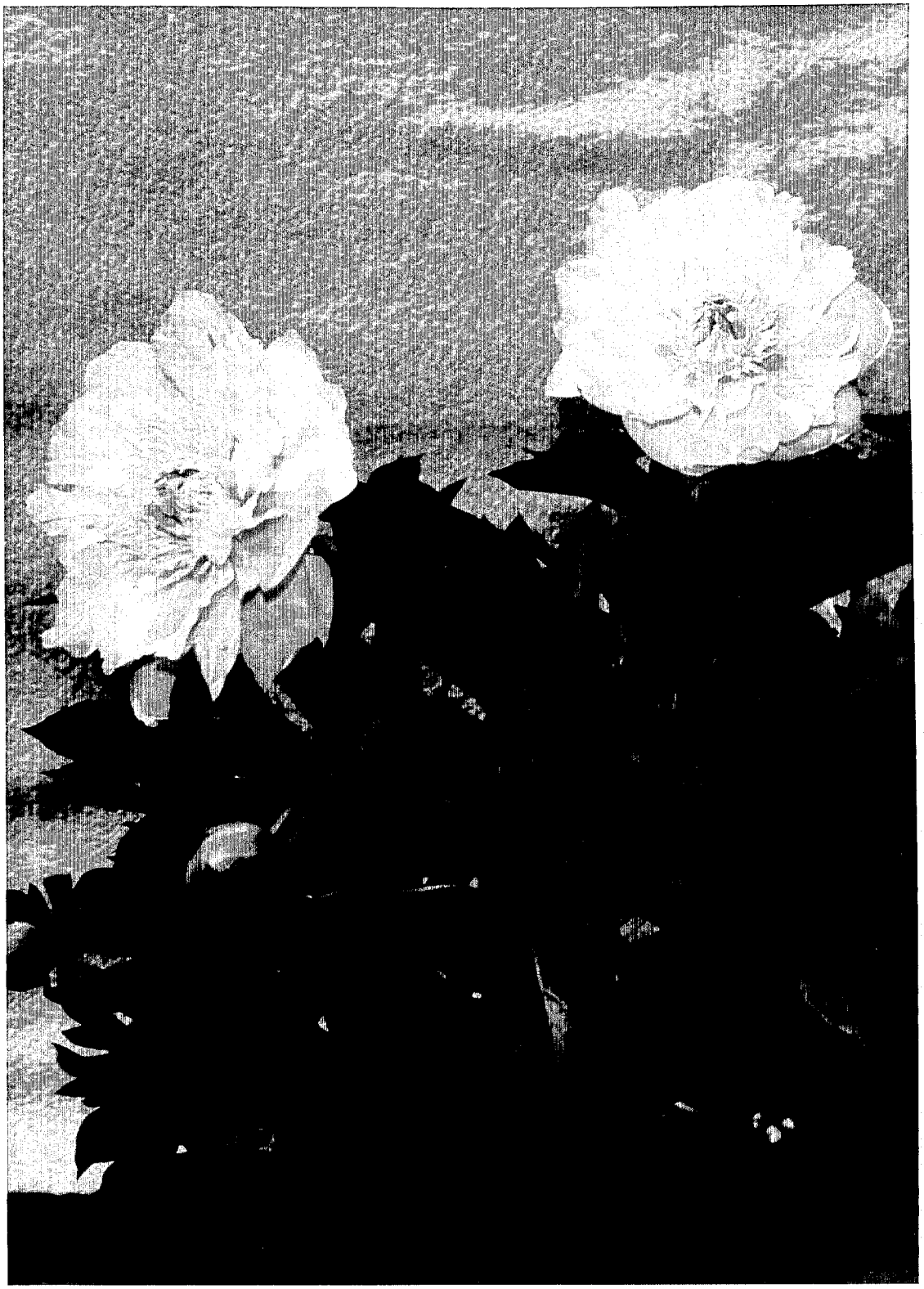

* * * * *